(12) United States Patent
Ebert et al.

(10) Patent No.: US 7,783,365 B2
(45) Date of Patent: Aug. 24, 2010

(54) IMPLANTABLE MEDICAL DEVICE CONDUCTOR INSULATION AND PROCESS FOR FORMING

(75) Inventors: Michael J. Ebert, Fridley, MN (US);
John L. Sommer, Coon Rapids, MN (US); Richard D. Ries, Stillwater, MN (US); Jordan D. Honeck, Maple Grove, MN (US); Pedro A. Meregotte, Vadnais Heights, MN (US); Kenneth R. Brennen, Zimmerman, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 10/909,518

(22) Filed: Aug. 2, 2004

(65) Prior Publication Data

US 2005/0004643 A1     Jan. 6, 2005

Related U.S. Application Data

(63) Continuation-in-part of application No. 10/407,653, filed on Apr. 4, 2003.

(60) Provisional application No. 60/371,995, filed on Apr. 11, 2002.

(51) Int. Cl.
    *A61N 1/00* (2006.01)
(52) U.S. Cl. .................................................. 607/122
(58) Field of Classification Search ................ 607/116, 607/119, 122; 174/107, 108, 126.2; 166/272.5; 428/379, 317.5; 528/353, 229
    See application file for complete search history.

(56) References Cited

U.S. PATENT DOCUMENTS

| | | |
|---|---|---|
| 3,035,583 A | 5/1962 | Stoltz et al. |
| 3,168,417 A | 2/1965 | Smith, Jr. et al. |
| 3,179,614 A | 4/1965 | Edwards |
| 3,179,630 A | 4/1965 | Endrey |
| 3,179,631 A | 4/1965 | Endrey |
| 3,179,632 A | 4/1965 | Hendrix |
| 3,179,633 A | 4/1965 | Endrey |
| 3,179,634 A | 4/1965 | Edwards |
| 3,287,311 A | 11/1966 | Edwards |
| 3,608,054 A | 9/1971 | Alvino et al. |
| 3,708,459 A * | 1/1973 | Lubowitz .................... 528/229 |
| 4,056,651 A | 11/1977 | Scola |
| 4,277,534 A * | 7/1981 | Flowers ..................... 428/379 |
| 4,627,439 A * | 12/1986 | Harris ..................... 166/272.5 |
| 4,789,589 A * | 12/1988 | Baxter ..................... 428/317.5 |

(Continued)

FOREIGN PATENT DOCUMENTS

EP         0539148 A      4/1993

(Continued)

OTHER PUBLICATIONS

Cobian, Ken, "Multiconductor Versus Conventional Lead Design: A Discussion," Technical Concept Paper, Medtronic, Inc., p. 1-4 (Apr. 1995).

(Continued)

*Primary Examiner*—George Manuel
(74) *Attorney, Agent, or Firm*—Carol F. Barry; Stephen W. Bauer

(57) ABSTRACT

An elongate medical electrical lead conductor includes a layer of hydrolytically stable polyimide formed thereover.

30 Claims, 4 Drawing Sheets

U.S. PATENT DOCUMENTS

| | | | |
|---|---|---|---|
| 4,922,607 A | 5/1990 | Doan et al. .................... 29/879 |
| 4,925,445 A | 5/1990 | Sakamoto et al. | |
| 4,939,317 A * | 7/1990 | Hostler ....................... 174/107 |
| 5,007,435 A | 4/1991 | Doan et al. ................. 128/784 |
| 5,069,226 A | 12/1991 | Yamauchi et al. | |
| 5,147,966 A | 9/1992 | St. Clair et al. | |
| 5,171,828 A | 12/1992 | Meterko et al. | |
| 5,184,627 A | 2/1993 | de Toledo | |
| 5,201,903 A | 4/1993 | Corbett, III et al. | |
| 5,210,174 A | 5/1993 | Tamai et al. | |
| 5,282,841 A | 2/1994 | Szyszkowski | |
| 5,298,331 A | 3/1994 | Kanakarajan et al. ....... 428/458 |
| 5,411,765 A | 5/1995 | Kanakarajan et al. .... 427/385.5 |
| 5,433,200 A | 7/1995 | Fleischhacker | |
| 5,445,859 A | 8/1995 | Lindegren et al. ............. 428/76 |
| 5,464,928 A | 11/1995 | Chang et al. | |
| 5,478,916 A | 12/1995 | Chang et al. | |
| 5,487,757 A | 1/1996 | Truckai et al. | |
| 5,502,157 A | 3/1996 | Chang et al. | |
| 5,573,533 A | 11/1996 | Strul | |
| 5,639,850 A * | 6/1997 | Bryant ....................... 528/353 |
| 5,669,383 A | 9/1997 | Johnson | |
| 5,741,883 A | 4/1998 | Bryant | |
| 5,760,341 A * | 6/1998 | Laske et al. ............. 174/126.2 |
| 5,775,327 A | 7/1998 | Randolph et al. | |
| 5,837,377 A | 11/1998 | Sheu et al. | |
| 5,845,396 A | 12/1998 | Altman et al. | |
| 5,851,227 A | 12/1998 | Spehr | |
| 5,897,583 A | 4/1999 | Meyer et al. | |
| 5,935,159 A | 8/1999 | Cross et al. | |
| 6,022,346 A | 2/2000 | Panescu et al. | |
| 6,048,959 A | 4/2000 | Bryant | |
| 6,133,408 A | 10/2000 | Chiu et al. .................. 528/353 |
| 6,141,576 A | 10/2000 | Littmann et al. | |
| 6,289,250 B1 | 9/2001 | Tsuboi et al. ............... 607/122 |
| 6,366,819 B1 | 4/2002 | Stokes | |
| 6,370,434 B1 | 4/2002 | Zhang et al. | |
| 6,374,141 B1 | 4/2002 | Sass | |
| 6,379,369 B1 | 4/2002 | Abrams et al. | |
| 6,402,689 B1 | 6/2002 | Scarantino et al. | |
| 6,434,430 B2 | 8/2002 | Borgersen et al. | |
| 6,489,562 B1 | 12/2002 | Hess et al. | |
| 6,493,591 B1 | 12/2002 | Stokes | |
| 6,553,265 B1 | 4/2003 | Fischer, Sr. | |
| 6,564,107 B1 | 5/2003 | Bodner et al. | |
| 6,606,521 B2 | 8/2003 | Paspa et al. | |
| 6,686,437 B2 | 2/2004 | Buchman et al. | |
| 6,919,422 B2 | 7/2005 | Gallucci et al. | |
| 6,979,319 B2 | 12/2005 | Manning et al. | |
| 7,627,382 B2 | 12/2009 | Minar et al. | |
| 2003/0216800 A1 | 11/2003 | Ebert et al. | |
| 2004/0215299 A1 | 10/2004 | Ebert et al. | |
| 2005/0004643 A1 | 1/2005 | Ebert et al. | |
| 2006/0229693 A1 | 10/2006 | Bauer et al. | |
| 2006/0271135 A1 | 11/2006 | Minar et al. | |
| 2007/0185556 A1 | 8/2007 | Williams et al. | |
| 2007/0208383 A1 | 9/2007 | Williams | |
| 2007/0233215 A1 | 10/2007 | Sommer et al. | |
| 2007/0250144 A1 | 10/2007 | Falk et al. | |
| 2007/0255377 A1 | 11/2007 | Marshall et al. | |
| 2008/0161898 A1 | 7/2008 | Bauer et al. | |
| 2008/0178449 A1 | 7/2008 | Huotari et al. | |
| 2008/0242964 A1 | 10/2008 | Horrigan et al. | |
| 2008/0243195 A1 | 10/2008 | Sommer et al. | |
| 2008/0243215 A1 | 10/2008 | Sommer et al. | |
| 2009/0248127 A1 | 10/2009 | Clemens et al. | |
| 2009/0306752 A1 | 12/2009 | Ebert et al. | |
| 2010/0114282 A1 | 5/2010 | Ebert et al. | |

FOREIGN PATENT DOCUMENTS

| | | |
|---|---|---|
| EP | 1192957 A2 | 4/2002 |
| FR | 2670677 A | 6/1992 |
| JP | 1990-159247 | 6/1990 |
| WO | WO 88/04940 | 7/1988 |
| WO | WO 2002/028476 A2 | 4/2002 |
| WO | WO 02/066539 A1 | 8/2002 |
| WO | WO 03/089045 A2 | 10/2003 |
| WO | WO 03/089045 A3 | 2/2005 |
| WO | WO 2006/017421 A1 | 2/2006 |
| WO | WO 2006/105066 A2 | 10/2006 |
| WO | WO 2006/105066 A3 | 5/2007 |
| WO | WO 2007/127620 A1 | 11/2007 |
| WO | WO 2008/094879 A1 | 8/2008 |
| WO | WO 2008/095059 A1 | 8/2008 |

OTHER PUBLICATIONS

Kreyenhagen, P. et al., "Evaluation of a New Insulation Material for Multiconductor Pacing Leads," Second International Symposium on Pacing Leads, vol. 46, p. 120 (Apr. 10-12, 1991) (Abstract).

Guidant Product Update "Continuous Improvement to Pulse Generator Headers" Jan. 27, 2006, 2 pgs.

NASA Technical Report # 1.71:LAR-15109-1, published Aug. 31, 1994; 15 pages.

Bryant, "Commercialization of LARC(Trademark)-SI Polyimide Technology," NASA Technical Reports Server (NTRS), May 4, 2008, Document ID 20080018690; POLYCOM 2008, May 4-7, 2008, Galveston, TX, United States; 3 pgs.

"Distinctive NASA Plastic Shows Great Promise for Industry", *Technology Transfer Week*, Aug. 29, 1995; p. 5.

"FDA Approves New Medtronic Left Heart Lead for Cardiac Resynchronization Therapy Devices," News Release, Medtronic, Inc., Minneapolis, MN, May 6, 2009; 3 pgs.

Hart, "A polyimide molecular composite," NASA Technical Reports Server (NTRS), Dec. 1995, Document ID 19960020773; The 1995 NASA-ODU American Society for Engineering Education (ASEE) Summer Faculty Fellowship Program, 80; Abstract only; 1 pg.

"Heart Disease" online. Medtronic, Inc., Minneapolis, MN, Copyright 2010 retrieved on Jan. 20, 2010. Retrieved from the Internet<URL:http://www.medtronic.comn/innovation/innovation-stories/heart-disease.html>; 1 pg.

Holloway et al., "Fabrication of adhesiveless lightweight flexible circuits using Langley Research Center soluble-imide 'LARC-SI' polyimide film (Proceedings Paper)," *SPIE Proceedings*, Jul. 9, 2002, Smart Structures and Materials 2002: Industrial and Commercial Applications of Smart Structures Technologies (Proceedings Volume), 4698: 293-303.

Hou et al., "Processing and Properties of IM7/LARC™-Si Polyimide Composites," *High Performance Polymers*, 1997, 9(4): 437-448.

Kiefer, "Predictions for Radiation Shielding Materials," NASA Technical Reports Server (NTRS), 2002, Document ID 20030020808. 19 pgs.

Meier, "Flawed Design: Patients at Risk; Repeated Defect in Heart Devices Exposes a History of Problems," *The New York Times*, New York, Oct. 20, 2005, retrieved on Jan. 20, 2010. Retrieved from the Internet in four parts: Part 1:<URL:http://query.nytimes.com/gst/fullpage.html?res=9405E7D9123FF933A15753C1A9639C8B63&sec=health&spon=&pagewanted=1>; Part 2: <URL:http://query.nytimes.com/gst/fullpage.html?res=9405E7D9123FF933A15753C1A9639C8B63&sec=health&spon=&pagewanted=2>; Part 3: <URL:http://query.nytimes.com/gst/fullpage.html?res=9405E7D9123FF 933A15753C1A9639C8B63&sec=health&spon=&pagewanted=3>; Part 4: <URL:http://query.nytimes.com/gst/fullpage.html?res=9405E7D9123FF 933A15753C1A9639C8B63&sec=health&spon=&pagewanted=4>; 12 pgs. total.

Miner et al. "The Wettability of LaRC Colorless Polyimide Resins on Casting Surfaces", Abstract # 235, 1997 American Chemical Society National Meeting, San Francisco, CA, Apr. 13-17, 1997; 8 pgs.

Moore, Janet, "New Medtronic heart device uses NASA 'super plastic'" StarTribune [online]. May 6, 2009 [retrieved on Jun. 5, 2009]. Retrieved from the Internet:<URL:http://www.startribune.com/business/44498642.html?page1&c=y>; 2 pgs.

Nicholson et al., "Influence of Molecular Weight on the Mechanical Performance of a Thermoplastic Glassy Polyimide," NASA Technical Reports Server (NTRS), Nov. 1999, Document ID 19990115891, Report No. NASA/TM-1999-209720; 33 pgs.

Nicholson et al., "Molecular Weight Effects on the Viscoelastic Response of a Polyimide," NASA Technical Reports Server (NTRS), 2000, Document ID 20040086732; SAMPE 2000: International SAMPE Symposium and Exhibition, "3A: Composites Durability," May 21-25, 2000, Long Beach, CA, United States; 15 pgs.

Nicholson et al., "The combined Influence of Molecular Weight and Temperature on the Aging andViscoelastic Response of a Glassy Thermoplastic Polyimide," NASA Technical Reports Server (NTRS), Sep. 2000, Document ID 20000096391, Report No. NASA/TM-2000-210312; 33 pgs.

Nicholson et al., "The Role of Molecular Weight and Temperature on the Elastic and Viscoelastic Properties of a Glassy Thermoplastic Polyimide," NASA Technical Reports Server (NTRS), Feb. 2001, Document ID 20010021135, Report No. NASA/TM-2001-210664; 22 pgs.

Schmidt et al., "Bipolar Pacemaker Leads: New Materials, New Technology", *Journal of Investigative Surgery*, Jan.-Feb. 1998; 11(1):75-81.

Varner et al., "Characterization of Polyimides by $^{13}$C and $^{1}$H Solid State Nuclear Magnetic Resonance", *Solid State Nuclear Magnetic Resonance*, Sep. 1998; 12(2-3):71-85.

Whitley et al., "Mechanical Properties of LARC(tm) SI Polymer for a Range of Molecular Weights," NASA Technical Reports Server (NTRS), Aug. 2000, Document ID 20000093315, Report No. NASA/TM-2000-210304; 36 pgs.

U.S. Appl. No. 12/683,561, filed Jan. 7, 2010, Ebert et al.

"Attain Ability® 4196: Steroid eluting, dual electrode, transvenous, over the wire, cardiac vein pacing lead" Technical Manual, 2009, Medtronic, Inc., Minneapolis, MN; 17 pgs.

Bruneau, "Featured Invention: Langley Soluble Imide," *Ask Magazine*, Summer 2006, Issue 24: 33-34.

Miner et al., "The Wettability of LaRC Colorless Polyimide Resins on Casting Surfaces," NASA Technical Reports Server (NTRS), 1997, Document ID 20040110380; 6 pgs.

Office Action dated Jan. 19, 2010 for U.S. Appl. No. 10/407,653; 12 pgs.

"Polymer Coats Leads on Implantable Medical Device," *Spinoff*, 2008; pp. 52-53.

* cited by examiner

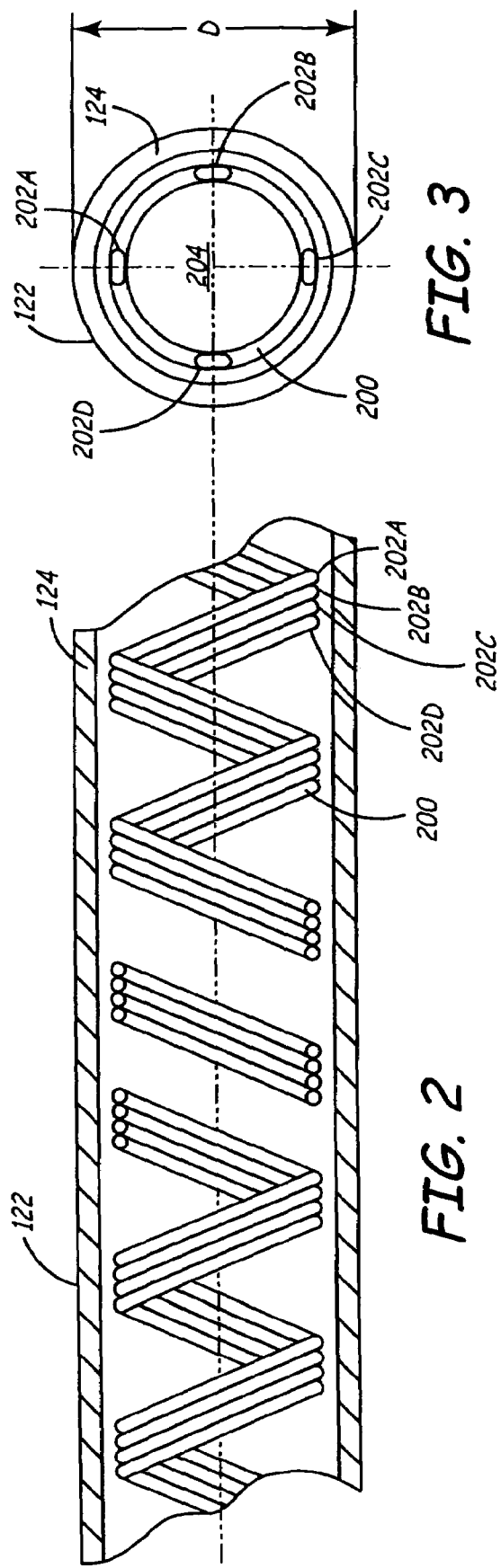

IMPLANTABLE MEDICAL DEVICE CONDUCTOR INSULATION AND PROCESS FOR FORMING

RELATED APPLICATION

This application is a continuation-in-part of U.S. patent application Ser. No. 10/407,653 filed on Apr. 4, 2003 and entitled "IMPLANTABLE MEDICAL DEVICE CONDUCTOR INSULATION AND PROCESS FOR FORMING", which claims priority and other benefits from U.S. Provisional Patent Application Ser. No. 60/371,995, filed Apr. 11, 2002, entitled "BIO-STABLE IMPLANTABLE MEDICAL DEVICE LEAD CONDUCTOR INSULATION AND PROCESS FOR FORMING", both of which are incorporated herein by reference in their entireties.

FIELD OF THE INVENTION

The present invention relates generally to implantable medical device leads for delivering therapy, in the form of electrical stimulation, and in particular, the present invention relates to conductor coil insulation in implantable medical device leads.

BACKGROUND OF THE INVENTION

Implantable medical electrical leads are well known in the fields of cardiac stimulation and monitoring, including neurological stimulation and cardiac pacing and cardioversion/defibrillation. In the field of cardiac stimulation and monitoring, endocardial leads are placed through a transvenous route to position one or more sensing and/or stimulation electrodes in a desired location within a heart chamber or interconnecting vasculature. During this type of procedure, a lead is passed through the subclavian, jugular, or cephalic vein, into the superior vena cava, and finally into a chamber of the heart or the associated vascular system. An active or passive fixation mechanism at the distal end of the endocardial lead may be deployed to maintain the distal end of the lead at a desired location.

It is highly desirable that implantable leads have the lowest possible profile while the insulation maintain sufficient integrity to electrically isolate one or more conductors of the leads over the life of the implanted lead.

BRIEF DESCRIPTION OF THE DRAWINGS

The following drawings are illustrative of particular embodiments of the invention and therefore do not limit its scope, but are presented to assist in providing a proper understanding of the invention. The drawings are not to scale (unless so stated) and are intended for use in conjunction with the explanations in the following detailed description. Embodiments of the present invention will hereinafter be described in conjunction with the appended drawings, wherein like numerals denote like elements, and:

FIG. 2 is a cross-sectional view of a lead of the exemplary device taken along cross-sectional lines II-II of FIG. 1;

FIG. 3 is a cross-sectional view of the lead of the exemplary device taken along cross-sectional lines III-III of FIG. 1;

DETAILED DESCRIPTION OF THE INVENTION

Figure 1:
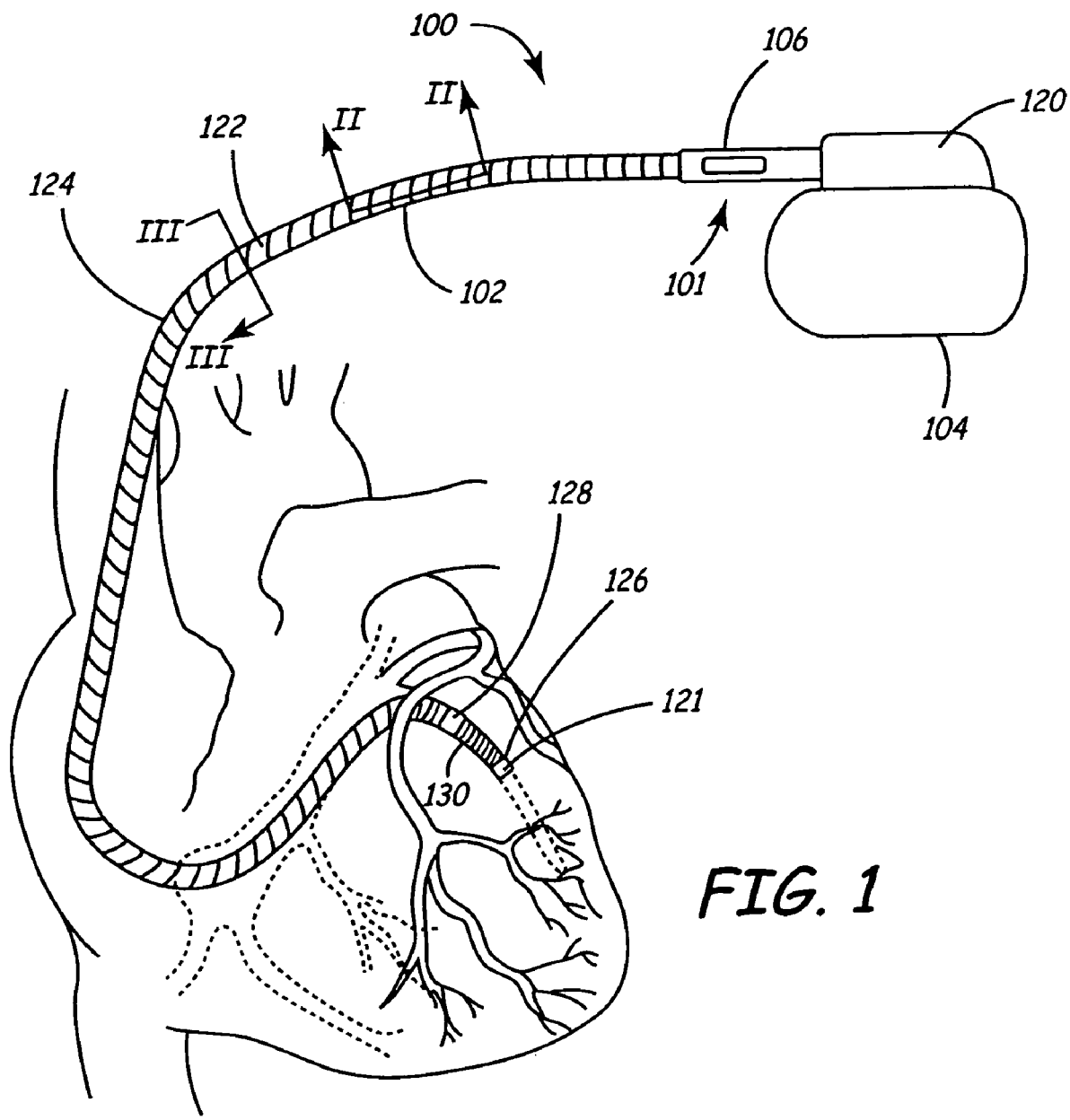
FIG. 1 is a schematic diagram of an exemplary implantable medical device in accordance with one embodiment of the present invention.

FIG. 1 is a schematic diagram of an exemplary implantable medical device in accordance with one embodiment of the present invention. As illustrated in FIG. 1, an implantable medical device 100 according to the present invention includes an implantable medical device lead 102 and an implantable medical device housing 104, such as an implantable cardioverter/defibrillator or pacemaker/cardioverter/defibrillator (PCD), for example, for processing cardiac data sensed through lead 102 and generating electrical signals in response to the sensed cardiac data for the provision of cardiac pacing, cardioversion and defibrillation therapies. A connector assembly 106 located at a proximal end 101 of lead 102 is insertable within a connector block 120 of housing 104 to electrically couple lead 102 with electronic circuitry (not shown) of housing 104.

Lead 102 includes an elongated lead body 122 that extends between proximal end 101 and a distal end 121 of lead 102. An outer insulative sheath 124 surrounds lead body 122 and is preferably fabricated of polyurethane, silicone rubber, a fluoropolymer or a combination thereof. Coiled wire conductors in accordance with one embodiment of the present invention are positioned within lead body 122, as will be described in detail below. Distal end 121 of lead 102 includes a proximal ring electrode 128 and a distal tip electrode 126, separated by an insulative sleeve 130. Proximal ring electrode 128 and distal tip electrode 126 are electrically coupled to connector assembly 106 by one or more coil conductors, or filars extending between distal end 121 and proximal end 101 of lead 102 in a manner shown, for example, in U.S. Pat. Nos. 4,922,607 and 5,007,435, incorporated herein by reference in their entireties.

Figure 6:
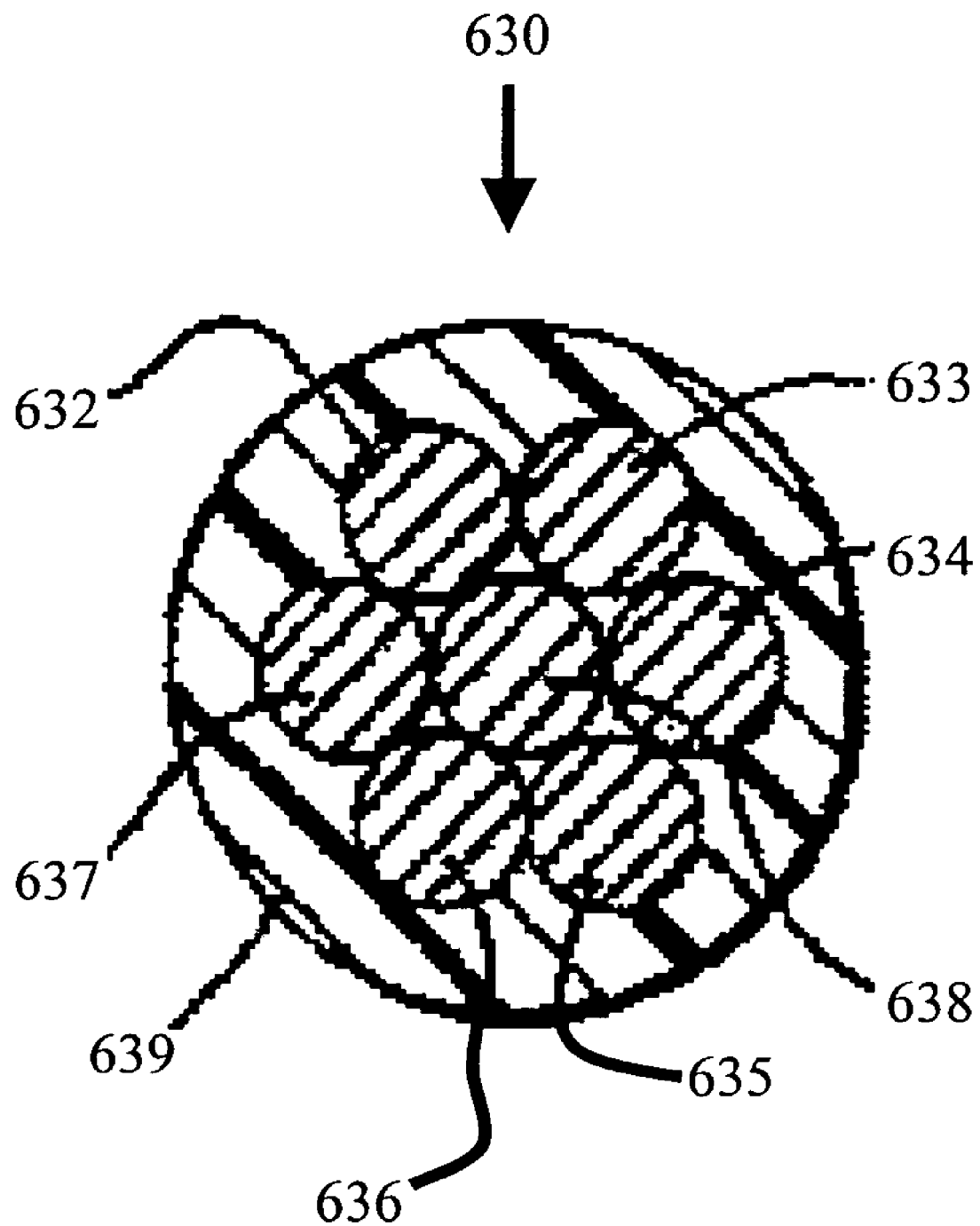
FIG. 6 is a cross-sectional view of an exemplary cabled wire conductor according to yet another embodiment of the present invention.

FIG. 2 is a cross-sectional view of a lead of the exemplary device taken along cross-sectional lines II-II of FIG. 1. As illustrated in FIG. 2, lead 102 of implantable medical device 100 includes a quadrafilar conductor coil 200 including four individual filars, or coiled wire conductors 202A, 202B, 202C and 202 extending within insulative sheath 124 of lead body 122. Coiled wire conductors 202A-202D electrically couple proximal ring electrode 128 and distal tip electrode 126 with connector assembly 106. It is understood that although the present invention is described throughout in the context of a quadrafilar conductor coil, having each of two electrodes electrically coupled to a connector assembly via two of the four individual coiled wire conductors, the present invention is not intended to be limit to application in a quadrafilar conductor coil. Rather, the lead conductor insulator of the present invention can be utilized in any conductor configuration, including the use of any number of conductor coils depending upon the number of desired electrodes, and would include the use of a single filar electrically coupling the electrode to the connector. Furthermore, as illustrated in FIG. 6, a lead conductor according to an alternate embodiment of the present invention may be in the form of a cable 630 including a plurality of bundled wire strands 632-638.

FIG. 3 is a cross-sectional view of the lead of the exemplary device taken along cross-sectional lines III-III of FIG. 1. As illustrated in FIGS. 2 and 3, each of the individual filars or coiled wire conductors 202A, 202B, 202C and 202D are parallel-wound in an interlaced manner to have a common outer and inner coil diameter. As a result, conductor coil 200 forms an internal lumen 204, which allows for passage of a stylet or guide wire (not shown) within lead 102 to direct insertion of lead 102 within the patient.

Alternately, lumen 204 may house an insulative fiber, such as ultrahigh molecular weight polyethylene (UHMWPE), liquid crystal polymer (LCP), polyester and so forth, or an insulated cable (i.e. cable 630 illustrated in FIG. 6) in order to allow incorporation of an additional conductive circuit and/or structural member to aid in chronic removal of lead 102 using traction forces. Such an alternate embodiment would require insertion and delivery of lead 102 to a final implant location using alternate means, such as a catheter, for example. Lumen 204 may also include an insulative liner (not shown), such as a fluoropolymer, polyimide, PEEK, for example, to prevent damage caused from insertion of a style/guidewire (not shown) through lumen 204.

Figure 4:
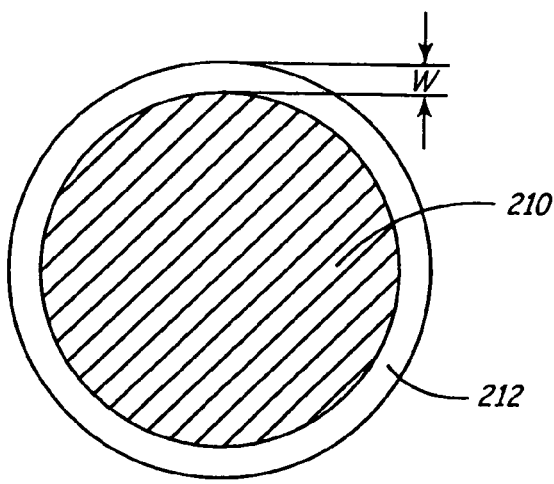
FIG. 4 is a cross-sectional view of a coiled wire conductor forming a filar of a multi-filar conductor coil according to one embodiment of the present invention.

FIG. 4 is a cross-sectional view of a coiled wire conductor forming a multi-filar conductor coil according to some embodiments of the present invention. As illustrated in FIG. 4, one or more of the individual coiled wire conductors 202A, 202B, 202C and 202D includes a conductor wire 210 surrounded by an insulative layer 212. According to the present invention, insulative layer 212 is formed of a hydrolytically stable polyimide, such as a Soluble Imide (SI) polyimide material, for example, (formerly known as Genymer, Genymer SI, and LaRC™ SI) as described in U.S. Pat. No. 5,639,850, issued to Bryant, and incorporated herein by reference in its entirety, to insulate conductor coils in implantable medical device leads. Such SI polyimide material is currently commercially available through license from NASA, for example. The thickness of the insulative layer 212 ranges from approximately 0.0001 inches up to approximately 0.0050 inches, forming a corresponding wall thickness W of the insulative layer 212. By utilizing the hydrolytically stable polyimide material as an insulative layer 212, the present invention provides an improved electrically insulating material that is hydrolytically stable in implantable (in vivo) applications.

According to one embodiment of the present invention, the insulative layer 212 is applied onto the conductor wire 210 in multiple coats, that is, layer 212 is comprised of multiple layers of a hydrolytically stable polyimide resulting in a desired wall thickness W. The coating is applied in such a way to provide a ductile, robust insulative layer that enables a single filar, i.e., coiled wire conductor, or multiple filar, i.e., coiled wire conductors, to be wound into a single wound conductor coil 200 of sizes ranging from an outer diameter D (FIG. 3) of 0.010 inches to 0.110 inches. For example, the coating process includes a solvent dip followed by an oven cure cycle to drive off the solvents and column 7, line 63 to column 8, line 14 of U.S. Pat. No. 4,056,651, which is incorporated herein by reference, describes a coating procedure which may be employed to manufacture embodiments of the present invention. According to an exemplary embodiment, wire 210, having a diameter between approximately 0.003 inch and approximately 0.005 inch, after being cleaned with an alkaline solution, undergoes 32 coating passes resulting in wall thickness W of approximately 0.0005 inch. For this embodiment the inventors have found that, in order to assure an adequate toughness and flexibility of each imidized coating layer, that is to prevent cracking upon subsequent processing of the coated wire, each layer should be exposed to a high enough temperature, for example an oven temperature between approximately 650° F. and approximately 850° F., for a sufficient time to drive off residual solvent. Thus, multiple coating passes forming insulative layer 212 on conductor wire 210 provides the ductility that is needed to make the coated conductor wire 210 into a conductor coil 200 that can withstand the long term flex requirements of an implantable lead. However, according to an alternate embodiment, one or more wire filars may be wound into a coiled configuration prior to applying a layer or layers of a hydrolytically stable polyimide. The inventors further contemplate spraying processes and extrusion processes known to those skilled in the art may also be employed to manufacture embodiments of the present invention.

The use of the hydrolytically stable polyimide insulative layer 212 according to embodiments of the present invention offers an exceptional dielectric strength for electrical insulation. Through flex studies on conductor coils coated with the SI polyimide, the inventors have found that the insulative layer 212 also has high flex properties in regards to stimulating lead conductor coil flex testing. The SI coating in various wall thicknesses will remain intact on the coil filar until the coil filar fractures as seen in conventional conductor coil flex studies (reference 10 million to 400 million flex cycles at various 90 degree radius bends).

Conductor coils 200 (FIG. 2) according to the present invention can include a single filar or multiple filars, with each filar being an individual circuit that could be associated with a tip electrode, a ring electrode, a sensor, and so forth. The present invention enables the use of multiple circuits in a single conductor coil, resulting in a downsizing of the implantable medical device. For example, there is approximately a 40 to 50 percent reduction in lead size between known bipolar designs, which traditionally utilized an inner coil and inner insulation, outer coil and outer insulation, to a lead design having multiple circuits in a single conductor coil having the insulative layer 212 according to the present invention.

Hydrolytically stable polyimides do not show a notable decrease in mechanical performance over time when immersed in an aqueous environment, such as an implant environment. Examples of polyimides considered to be hydrolytically stable may have the following general recurring structure:

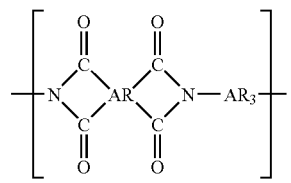

Wherein AR is either AR1 or AR2 that represent different dianhydrides and wherein either AR1 or AR2 is represented by the following general formula including isomeric variations thereof:

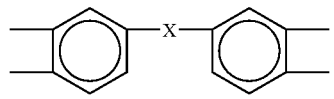

Wherein X can be represented by $CH_2$, $CH_3$—C—$CH_3$, O (Oxygen), C=O (carbonyl), S (sulfide), $SO_2$ (sulfonyl), $CF_3$—C—$CF_3$ (hexafluoropropane derivative), or no element (e.g., 3,4,3',4'-biphenyltetracarboxylic dianhydride (BPDA)) and wherein AR3 is a diamine and can be represented by the following formula:

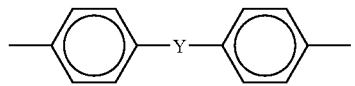

including, as shown below, isomeric variations thereof:

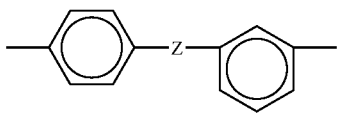

Wherein Y and Z can be represented by $CH_2$, $CH_3$—C—$CH_3$, O, C=O, S, $SO_2$, or $CF_3$—C—$CF_3$. Similar to the dianhydride (e.g., AR1, AR2), the polyimide may be composed of one or more diamines (AR3) or combinations of the above structures. The resultant polyimides may be endcapped by a number of chemicals know to the industry (e.g., phthalic anhydride) and the polyimide or the polyamic acid precursor may be supplied in a variety of solvents known to those in the industry (e.g., N,N dimethylacetamide (DMAc), dimethyl foramide (DMF), N-methylpyrrolidinone (NMP)). The hydrolytically stable polyimide may utilize mole ratios of the dianhydrides and may possess offsets (excess of diamine to dianhydride) similar to those known to the industry. The polyimides may also be further modified by incorporating specialized constituents such as crosslinking agents (e.g., nadic groups), fluorine containing groups (e.g., $CF_3$, $SF_5$, hexafluoropropane), or processing aids commonly known to those in the industry. Examples of hydrolytically stable polyimides suitable for embodiments of the present invention are:

1. LaRC™ SI, wherein:
AR1: X is O (4,4'-oxydiphthalic anhydride, ODPA)
AR2: X is no element (3,4,3',4'-biphenyltetracarboxylic dianhydride, BPDA)
AR3: Z is O (3,4'-oxydianiline, ODA)

2. A polyimide described in NASA technical report #NAS 1.71:LAR-15109-1 (published Aug. 31, 1994), wherein:
AR1: X is O (4,4'-oxydiphthalic anhydride, ODPA)
AR2: X is C=O (3,3',4,4'-benzophenonetetracarboxylic dianhydride, BTDA)
AR3: Z is O (3,4'-oxydianiline, ODA)

3. A polyimide described in U.S. Pat. No. 5,171,828, wherein:
AR1: X is O (4,4'-oxydiphthalic anhydride, ODPA)
AR2: X is no element (3,4,3',4'-biphenyltetracarboxylic dianhydride, BPDA)
AR3: Y is O (4,4'-oxydianiline, ODA)

4. LaRC™ TPI, wherein:
AR: X is C=O (3,3',4,4'-benzophenonetetracarboxylic dianhydride, BTDA)
AR3: Z is C=O (m-BDA)

Figure 5:
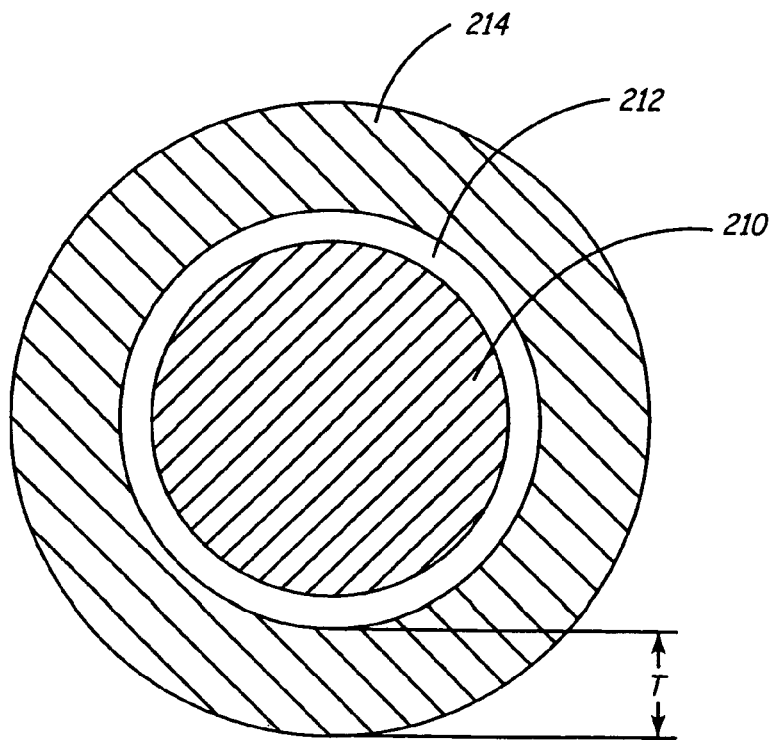
FIG. 5 is a cross-sectional view of a coiled wire conductor forming a filar of a multi-filar conductor coil according to another embodiment of the present invention.

FIG. 5 is a cross-sectional view of a coiled wire conductor forming a multi-filar conductor coil according to another embodiment of the present invention. The insulative layer 212 of hydrolytically stable polyimide according to embodiments of the present invention can be utilized as a stand-alone insulation on a filer or as an initial layer of insulation followed by an additional outer layer as redundant insulation to enhance reliability. For example, according to an embodiment of the present invention illustrated in FIG. 5, in addition to conductor wire 210 and insulative layer 212, one or more of the individual coiled wire conductors 202A, 202B, 202C and 202D includes an additional outer insulative layer 214, formed of known insulative materials, such as ETFE, for example, to enhance reliability of the lead. According to the present invention, insulative layer 214 generally has a thickness T between approximately 0.0005 and 0.0025 inches, for example, although other thickness ranges are contemplated by the present invention. Since the outermost insulative layer, i.e., insulative layer 214, experiences more displacement during flex of lead 102 than insulative layer 212, it is desirable for insulative layer 214 to be formed of a lower flex modulus material than insulative layer 212, such as ETFE.

By utilizing the insulative layer 212 of the present invention, the stimulating lead is reduced in diameter, and is more robust in regards to mechanical flex and electrical insulation. The insulative layer 212 provides an extremely long-term flex-life performance associated with the ductility of the hydrolytically stable polyimide coating over conductor wires such as MP35N, used on conductor coils. These improved properties are related to the unique process of the multiple pass application of the hydrolytically stable polyimide.

The resulting insulative layer 212 provides a highly reliable insulating and mechanically robust coating over implantable stimulating leads.

While an insulative layer formed only of ETFE tends to be susceptible to creep, insulative layer 212 of the present invention, which is formed of hydrolytically stable polyimide, is mechanically more robust, hydrolytically stable and possesses exceptionally dielectric properties, making the hydrolytically stable polyimide desirable for long-term implant applications. The use of a thin layer of hydrolytically stable polyimide coating on conventional MP35N alloy coil filars may also act as a protective barrier to reduce the incidence of metal induced oxidation seen on some polyurethane medical device insulations.

FIG. 6 is a radial cross-section of an exemplary cabled wire conductor according to yet another embodiment of the present invention. FIG. 6 illustrates cable 630 including bundled wire strands 632-637 formed about a core wire strand 638, any or all of which strands may be formed from a Co—Ni—Cr—Mo alloy, MP35N, or any other conductive corrosion-resistant and biocompatible material of sufficient strength and toughness for incorporation into a medical electrical lead; a diameter of each wire strand in various embodiments is between approximately 0.0005 inch and 0.005 inch. Using a conventional stranding machine, wire strands 632-638 are each tightly bundled in a cable-like fashion; a lay or pitch of stranding is typically between 0.3 inch and 0.6 inch. As is further illustrated in FIG. 6, cable 630 includes an insulating layer 639 surrounding bundled wire strands 632-638, which is formed from a hydrolytically stable polyimide, examples of which have been previously described. It should be noted that, although FIG. 6 illustrates insulating layer 639 surrounding the plurality of wire strands as bundled, according to an alternate embodiment, one or more of each of the individual wire strands include an insulating layer of a hydrolytically stable polyimide, for example as illustrated in FIG. 4, and layer 639 may or may not be included. Another type of cable configuration, which may include a hydrolytically stable polyimide insulating layer, is described in U.S. Pat. No. 5,760,341, issued to Laske et al., the teachings of which are incorporated herein.

According to one embodiment, layer 639 may be applied to the bundled wire strands 632-638 by passing them through a polyamic acid solution and then heating the strands to a temperature sufficient to fully imidize the polyimide; likewise layer 212 may be applied to conductor 210 in a similar manner. As previously described, multiple coating passes may form layers 630 and 212. According to an alternate embodiment an extrusion process may be used to apply layer 639 or layer 212; the type of polyimide described by Example 4, above, may be particularly suitable for extrusion. According to yet another embodiment a second layer of another, insulative material is formed over layer 639, for example a layer of ETFE as described in conjunction with FIG. 5.

While a particular embodiment of the present invention has been shown and described, modifications may be made. It is therefore intended in the appended claims to cover all such changes and modifications, which fall within the true spirit and scope of the invention.

What is claimed is:

1. A method for manufacturing a medical electrical lead, the method comprising the steps of applying to an elongate lead conductor a liquid comprising a polyamic acid precursor and forming a layer of hydrolytically stable polyimide on the elongate lead conductor; wherein the hydrolytically stable polyimide is defined by the following chemical structure:

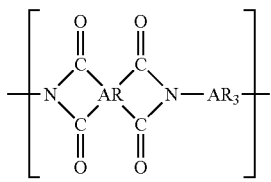

wherein AR is selected from AR1, AR2, and combinations thereof, wherein AR1 and AR2 represent different dianhydrides; with the proviso that the polyimide is not a copolyimide that includes 4,4'-oxydiphthalic anhydride as AR1, and 3,4,3',4'-biphenyltetracarboxylic dianhydride as AR2, and 3,4'-oxydianiline as AR3.

2. The method of claim 1, wherein the method comprises a dip coating process.

3. The method of claim 1, wherein the method comprises a spray coating process.

4. The method of claim 1, wherein the method comprises an extrusion process.

5. The method of claim 1, further comprising the step of forming an additional layer of hydrolytically stable polyimide on the lead conductor.

6. The method of claim 1, further comprising the step of forming multiple additional layers of hydrolytically stable polyimide on the lead conductor.

7. The method of claim 1, further comprising the step of forming an insulative layer of material over the layer of hydrolytically stable polyimide.

8. The method of claim 7, wherein the insulative layer comprises a fluoropolymer.

9. The method of claim 1, further comprising the step of winding the lead conductor into a coil.

10. The method of claim 9, wherein the step of winding precedes the step of forming.

11. The method of claim 9, wherein the step of winding follows the step of forming.

12. The method of claim 1, further comprising the step of bundling the conductor with a plurality of other lead conductors to form a cable.

13. The method of claim 1, wherein the lead conductor comprises a cable formed by a bundle of wires.

14. A medical electrical lead, comprising a conductor including a layer of hydrolytically stable polyimide formed thereover; wherein the hydrolytically stable polyimide is defined by the following chemical structure:

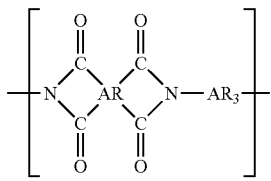

wherein AR is selected from AR1, AR2, and combinations thereof, wherein AR1 and AR2 represent different dianhydrides; with the proviso that the polyimide is not a copolyimide that includes 4,4'-oxydiphthalic anhydride as AR1, and 3,4,3',4'-biphenyltetracarboxylic dianhydride as AR2, and 3,4'-oxydianiline as AR3.

15. The lead of claim 14, wherein the conductor further includes another layer of hydrolytically stable polyimide formed thereover.

16. The lead of claim 14, wherein the conductor further includes multiple additional layers of hydrolytically stable polyimide formed thereover.

17. The lead of claim 14, wherein the conductor further includes a plurality of bundled wire strands extending within the layer of hydrolytically stable polyimide.

18. The lead of claim 14, wherein the conductor is a one of a plurality of bundled wire strands.

19. The lead of claim 14, wherein the conductor is a one of a plurality of coiled wire filars.

20. The lead of claim 14, wherein the conductor further includes a layer of fluoropolymer formed over the layer of hydrolytically stable polyimide.

21. The medical electrical lead of claim 14, wherein another insulative layer comprises ETFE.

22. The medical electrical lead of claim 14 further comprising:
an insulative liner of PEEK.

23. An implantable medical device electrical lead comprising:
a lead body extending from a proximal end to a distal end and having a connector assembly at the proximal end and electrodes at the distal end;
a multi-filar conductor coil extending through the lead body between the proximal end connector assembly and the distal end electrodes;
an insulative layer coupled to the multi-filar conductor coil, the insulative layer comprising a hydrolytically stable polyimide material,
wherein the hydrolytically stable polyimide is defined by the following chemical structure:

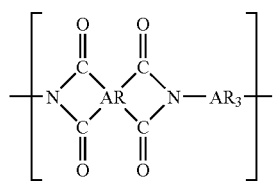

wherein AR is selected from AR1, AR2, and combinations thereof, wherein AR1 and AR2 represent different dianhydrides; with the proviso that the polyimide is not a copolyimide that includes 4,4'-oxydiphthalic anhydride as AR1, and 3,4,3',4'-biphenyltetracarboxylic dianhydride as AR2, and 3,4'-oxydianiline as AR3.

24. An implantable medical device electrical lead comprising:
a lead body extending from a proximal end to a distal end and having a connector assembly at the proximal end and electrodes at the distal end;
a cable conductor extending through the lead body between the proximal end connector assembly and the distal end electrodes;

an insulative layer coupled to the cable conductor, the insulative layer comprising a hydrolytically stable polyimide material,
wherein the hydrolytically stable polyimide is defined by the following chemical structure:

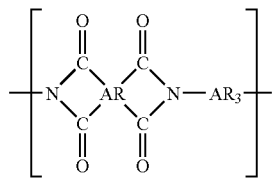

wherein AR is selected from AR1, AR2, and combinations thereof, wherein AR1 and AR2 represent different dianhydrides; with the proviso that the polyimide is not a copolyimide that includes 4,4'-oxydiphthalic anhydride as AR1, and 3,4,3',4'-biphenyltetracarboxylic dianhydride as AR2, and 3,4'-oxydianiline as AR3.

25. A medical electrical lead comprising:
one or more conductors, each conductor surrounded by an insulative layer comprising hydrolytically stable polyimide, wherein each conductor is configured to perform one of therapy delivery and sensing of data associated with a patient; wherein the hydrolytically stable polyimide is defined by the following chemical structure:

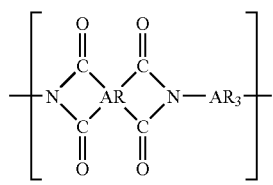

wherein AR is selected from AR1, AR2, and combinations thereof, and wherein AR1 and AR2 represent different dianhydrides.

26. A medical electrical lead comprising:
one or more conductors, each conductor surrounded by an insulative layer, wherein each conductor is configured to perform one of therapy delivery and sensing of data associated with a patient, wherein the insulative layer comprises hydrolytically stable polyimide defined by the following chemical structure:

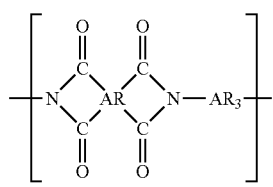

wherein AR is selected from AR1, AR2, and combinations thereof, wherein AR1 and AR2 represent different dianhydrides; with the proviso that the polyimide is not a copolyimide that includes 4,4'-oxydiphthalic anhydride as AR1, and 3,4,3',4'-biphenyltetracarboxylic dianhydride as AR2, and 3,4'-oxydianiline as AR3.

27. The medical electrical lead of claim 26, wherein AR1 and AR2 are represented by the chemical structure:

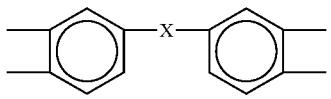

wherein X is one of $CH_2$, $CH_3$—C—$CH_3$, O(Oxygen), C=O (carbonyl), S(sulfide), $SO_2$(sulfonyl), $CF_3$—C—$CF_3$ (hexafluoropropane derivative), and no element.

28. The medical electrical lead of claim 27, wherein AR3 is a diamine represented by one of:

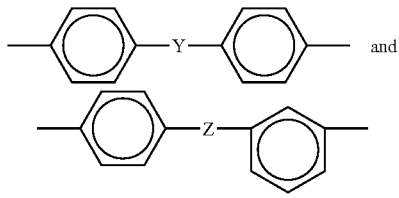

wherein Y and Z are one of $CH_2$, $CH_3$—C—$CH_3$, O, C=O, S, $SO_2$, and $CF_3$—C—$CF_3$.

29. A method for manufacturing a medical electrical lead, the method comprising the steps of applying to an elongate lead conductor a liquid comprising a polyamic acid precursor and forming a layer of hydrolytically stable polyimide on the elongate lead conductor; wherein the hydrolytically stable polyimide is defined by the following chemical structure:

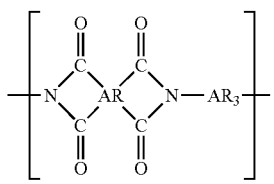

wherein AR is selected from AR1, AR2, and combinations thereof, and wherein AR1 and AR2 represent different dianhydrides.

30. A medical electrical lead, comprising a conductor including a layer of hydrolytically stable polyimide formed thereover; wherein the hydrolytically stable polyimide is defined by the following chemical structure:

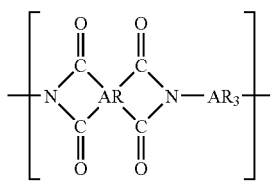

wherein AR is selected from AR1, AR2, and combinations thereof, and wherein AR1 and AR2 represent different dianhydrides.

* * * * *